US012631542B2

(12) United States Patent
Ahn

(10) Patent No.: US 12,631,542 B2
(45) Date of Patent: May 19, 2026

(54) CONDENSATION PARTICLE COUNTER AND SYSTEM INCLUDING SAME

(71) Applicant: Kang-Ho Ahn, Seoul (KR)

(72) Inventor: Kang-Ho Ahn, Seoul (KR)

(*) Notice: Subject to any disclaimer, the term of this patent is extended or adjusted under 35 U.S.C. 154(b) by 294 days.

(21) Appl. No.: 18/390,912

(22) Filed: Dec. 20, 2023

(65) Prior Publication Data

US 2025/0208018 A1        Jun. 26, 2025

(51) Int. Cl.
| | |
|---|---|
| *G01N 15/1409* | (2024.01) |
| *A61B 10/00* | (2006.01) |
| *B01L 3/00* | (2006.01) |
| *G01N 1/20* | (2006.01) |
| *G01N 1/40* | (2006.01) |
| *G01N 15/14* | (2024.01) |

(52) U.S. Cl.
CPC ...... *G01N 15/1409* (2024.01); *A61B 10/0038* (2013.01); *A61B 10/0096* (2013.01); *B01L 3/502715* (2013.01); *G01N 1/2035* (2013.01); *G01N 1/40* (2013.01); *G01N 2015/1486* (2013.01); *G01N 2015/1493* (2013.01)

(58) Field of Classification Search
CPC ....... G01N 15/1409; G01N 2015/1486; G01N 2015/1493; G01N 1/2035; G01N 1/40; B01L 3/502715; A61B 10/0038; A61B 10/0096
USPC ....................................................... 73/64.56
See application file for complete search history.

(56) References Cited

U.S. PATENT DOCUMENTS

| | | | | | |
|---|---|---|---|---|---|
| 4,790,650 | A | * | 12/1988 | Keady ................. | G01N 15/065 |
| | | | | | 356/37 |
| 6,330,060 | B1 | * | 12/2001 | Flagan .............. | G01N 15/0211 |
| | | | | | 356/370 |
| 6,829,044 | B2 | * | 12/2004 | Liu ...................... | G01N 15/065 |
| | | | | | 250/222.2 |
| 7,647,811 | B2 | * | 1/2010 | Wei ..................... | G01N 15/065 |
| | | | | | 73/23.31 |

(Continued)

FOREIGN PATENT DOCUMENTS

| | | | | | |
|---|---|---|---|---|---|
| AT | | 519132 | B1 | * | 4/2018 ........... G01N 1/2247 |
| AT | | 519912 | A1 | * | 11/2018 ........... G01N 15/065 |

(Continued)

OTHER PUBLICATIONS

Stolzenburg et al., An Ultrafine Aerosol Condensation Nucleus Counter, Aerosol Science and Tehnology,Journal homepage: www.tandfonline.com/journals/uast20, 14:48-65 (1991) (Year: 1991).*

(Continued)

*Primary Examiner* — Stephanie E Bloss
*Assistant Examiner* — Kevin C Butler
(74) *Attorney, Agent, or Firm* — Secant IP, PLLC

(57) ABSTRACT

A condensation particle counter includes: a saturator formed therein with a first flow path for supplying vapor to air introduced from an outside; a condenser formed therein with a second flow path in which the air and the vapor introduced from the first flow path are condensed; and a detector for detecting droplets condensed in the condenser, wherein the second flow path is provided with a guiding portion for guiding condensate flowing downward along an inner surface of the second flow path to flow into the saturator.

18 Claims, 10 Drawing Sheets

(56)                References Cited

U.S. PATENT DOCUMENTS

| | | | | |
|---|---|---|---|---|
| 7,724,368 | B2 * | 5/2010 | Ahn | G01N 15/065 356/336 |
| 7,777,868 | B2 * | 8/2010 | Blackford | G01F 1/661 356/336 |
| 8,603,247 | B2 * | 12/2013 | Liu | G01N 15/065 356/37 |
| 10,352,844 | B2 * | 7/2019 | Pariseau | G01N 15/1459 |
| 10,792,694 | B2 * | 10/2020 | Gorbunov | B05C 3/02 |
| 11,320,360 | B2 * | 5/2022 | Lumpkin | G01N 15/1434 |
| 2004/0012772 | A1 * | 1/2004 | Ahn | G01N 15/065 356/37 |
| 2009/0009749 | A1 * | 1/2009 | Ahn | G01N 15/065 356/37 |
| 2017/0350801 | A1 * | 12/2017 | Knollenberg | G01N 15/065 |
| 2020/0072724 | A1 * | 3/2020 | Knollenberg | G01N 1/02 |
| 2025/0208018 | A1 * | 6/2025 | Ahn | G01N 15/1409 |

FOREIGN PATENT DOCUMENTS

| | | | | |
|---|---|---|---|---|
| AT | 519913 A1 | * | 11/2018 | G01N 21/15 |
| CN | 111474105 A | * | 7/2020 | G01N 15/0205 |
| CN | 109310944 B | * | 5/2021 | G01N 15/065 |
| CN | 113677977 A | * | 11/2021 | G01N 15/06 |
| CN | 114062229 A | * | 2/2022 | G01N 15/10 |
| CN | 114894677 A | * | 8/2022 | G01N 15/0266 |
| CN | 116359104 A | * | 6/2023 | G01N 15/1434 |
| DE | 102005001992 A1 | * | 7/2006 | G01N 15/065 |
| DE | 112016005270 A5 | * | 7/2018 | G01N 1/2247 |
| DE | 112019000599 A5 | * | 10/2020 | G01N 15/065 |
| EP | 1953523 A2 | * | 8/2008 | G01N 15/065 |
| EP | 2012108 A2 | * | 1/2009 | G01N 15/065 |
| JP | 5883641 B2 | * | 3/2016 | G01N 15/065 |
| KR | 100497184 B1 | * | 6/2005 | |
| KR | 101885428 B1 | * | 8/2018 | B01D 5/006 |
| KR | 20210018259 A | * | 2/2021 | G01N 1/2252 |
| KR | 102359752 B1 | * | 2/2022 | G01N 15/14 |
| KR | 20250140206 A | * | 9/2025 | G01N 21/64 |
| TW | 202028720 A | * | 8/2020 | G01N 15/1434 |

OTHER PUBLICATIONS

Bhilare et al., Modification in gate valve using flexible membrane pipe for flow measurment, SN Applied Sciences, (2021) 3:852, https://doi.org/10.1007/s42452-021-04831-x (Year: 2021).*

Iida et al., Effect of Working Fluid on Sub-2 nm Particle Detection with a Laminar Flow Ultrafine Condensation Particle Counter, Aerosol Science and Technology, 43:81-96, 2009 (Year: 2009).*

Ensor et al., Aerosol Science and Technology: History and Reviews, RTI International, https://doi.org/10.3768/rtipress.2011.bk.0003.1109, 2011 (Year: 2011).*

Guo et al., Numerical simulation on the effects of flow parameters on the detection performance of a self-developed condensation particle counter, https://doi.org/10.1007/s11051-023-05865-5, J Nanopart Res (2023) 25:218 (Year: 2023).*

* cited by examiner

FIG. 2          # FIG. 3
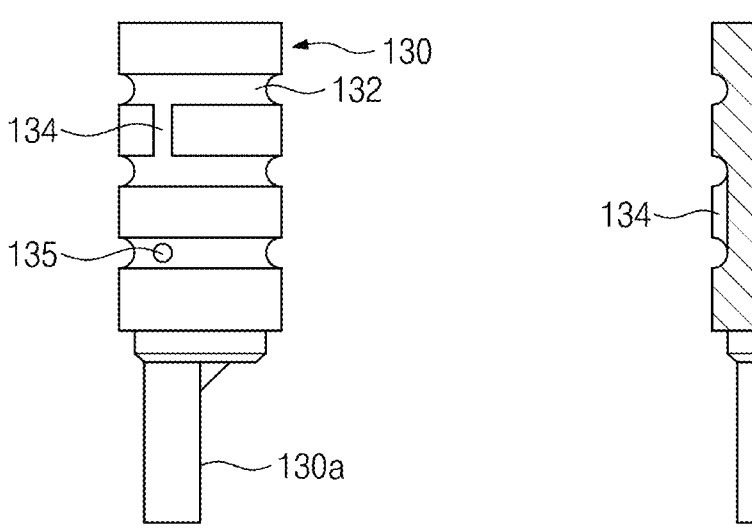
FIG. 4
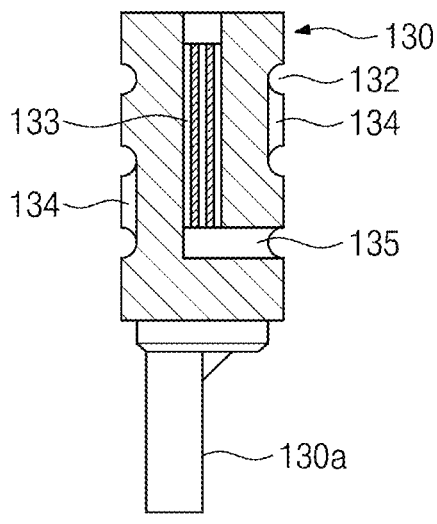

CONDENSATION PARTICLE COUNTER AND SYSTEM INCLUDING SAME

BACKGROUND OF THE INVENTION

1. Field of the Invention

The present invention relates to a condensation particle counter and a system including the same, and more particularly, to a condensation particle counter and a system including the same to supply vapor to the air until a saturated state, condense the vapor to create droplets having nano-particles contained in the air as condensation nuclei, and optically detect largely grown droplets, so that the number and size of the nano-particles contained in the air can be measured.

2. Description of the Related Art

A condensation particle counter refers to the most widely used device capable of measuring the concentration of nano-particles in real time. The condensation particle counter supersaturates a gas containing nano-particles, condenses the supersaturated vapor to create droplets having nano-particles as condensation nuclei, and optically detects largely grown droplets, so as to measure the number of nano-particles.

In order to continuously create supersaturated vapor, the condensation particle counter is required to maintain an amount of evaporated fluid in a saturator constant. When the amount of evaporated fluid evaporated in the saturator is the same as the amount of condensate condensed in the condenser, the flow rate of the evaporated fluid inside the saturator is maintained constant. However, when the amount of condensate condensed in the condenser is greater than the amount of evaporated fluid evaporated in the saturator, the flow rate of the evaporated fluid in the saturator is continuously increased. When the above situation continues, the amount of evaporated fluid in the saturator may exceed the appropriate level, thereby causing problems in a system operation. Thus, the evaporated fluid is required to be discharged to the outside. On the contrary, when the amount of evaporated fluid in the saturator is less than the amount of condensate condensed in the condenser, the amount of evaporated fluid inside the saturator is decreased as time flows. In this case, a predetermined amount of liquid is required to be supplied from the outside to continuously operate the system.

In addition, the supersaturated vapor may be condensed in the condenser. In this process, condensate is formed on a wall of the condenser, and the condensate flows downward along the wall by gravity and adheres to an end of the condenser. When the condensate adhering to the end of the condenser is not quickly discharged to the outside, the size of droplets may be increased and the droplets may be pushed back into the condenser due to friction with the introduced air. The droplets flow into an optical unit mounted to an upper portion of the condenser, and the optical unit may be wet by the droplets, thereby causing problems in the system operation.

In addition, in order to saturate the air in the saturator, the contact area between the liquid-containing porous material and the air is required to be expanded. When the porous material is increased in size and length for the expanded contact area, the size of the saturator is required to be increased.

In addition, conventional condensation particle counters may measure the number of nano-particles by optically detecting droplets, but may not measure the size of nano-particles surrounded by condensate.

SUMMARY OF THE INVENTION

The present invention provides a condensation particle counter capable of quickly discharging condensate generated during condensation of supersaturated vapor to the outside of a condenser.

In addition, the present invention provides a condensation particle counter capable of maintaining the flow rate of a working fluid stored in a condenser constant.

In addition, the present invention provides a condensation particle counter capable of providing a saturator in a small volume and increasing the contact area with air within the saturator.

In addition, the present invention provides a condensation particle counting system capable of optically detecting droplets and measuring the number and size of nano-particles.

The condensation particle counter according to the embodiments of the present invention includes: a saturator formed therein with a first flow path for supplying vapor to air introduced from an outside; a condenser formed therein with a second flow path in which the air and the vapor introduced from the first flow path are condensed; and a detector for detecting droplets condensed in the condenser, wherein the second flow path is provided with a guiding portion for guiding condensate flowing downward along an inner surface of the second flow path to flow into the saturator.

In addition, the condensation particle counting system according to the embodiments of the present invention includes: a plurality of condensation particle counters; and a control unit for individually controlling the condensation particle counters, wherein each of the condensation particle counters includes: a saturator for heating an inside thereof to generate vapor and supplying the vapor to air introduced from an outside; and a condenser for cooling an inside thereof to condense the air and the vapor introduced from the saturator, wherein the control unit controls each of the condensation particle counters to have a different heating temperature of the saturator and a different cooling temperature of the condenser.

According to the present invention, condensate is guided to a discontinuous surface formed on a wall of a condensation pipe and quickly discharged into a saturator along the discontinuous surface, so that the condensate can be blocked from being introduced into a detector along the air flow.

In addition, according to the present invention, a vertical level of a working fluid in a storage tank is kept the same as a vertical level of a working fluid in a saturation container, and a vertical level of the working fluid in the storage tank is maintained at a constant height through a vertical level control block, so that the vertical level of the working fluid in the saturation container can be maintained constant.

In addition, according to the present invention, sample air is circulated around an absorber several times along an outer flow path formed on an outer surface of the absorber and then flows into an inner flow path, so that the contact area with air can be increased in a small-sized absorber.

In addition, according to the present invention, saturation degrees inside condensers may be set differently, so that a particle having a predetermined size or greater can be detected from each detector.

BRIEF DESCRIPTION OF THE DRAWINGS

FIG. 2 is a drawing showing an outer surface of an absorber according to one embodiment of the present invention.

FIG. 3 is a sectional view showing the absorber of FIG. 2.

FIG. 4 is a sectional view showing an absorber according to another embodiment of the present invention.

DETAILED DESCRIPTION OF THE INVENTION

Hereinafter, exemplary embodiments of the present invention will be described in detail with reference to the accompanying drawings. However, the technical idea of the present invention is not limited to the exemplary embodiments described herein and may be embodied in other forms. Further, the embodiments are provided to enable contents disclosed herein to be thorough and complete and provided to enable those skilled in the art to fully understand the idea of the present invention.

In the specification herein, when one component is mentioned as being on other component, it signifies that the one component may be placed directly on the other component or a third component may be interposed therebetween. In addition, in drawings, thicknesses of layers and areas may be exaggerated to effectively describe the technology of the present invention.

In addition, although terms such as first, second and third are used to describe various components in various embodiments of the present specification, the components will not be limited by the terms. The above terms are used merely to distinguish one component from another. Accordingly, a first component referred to in one embodiment may be referred to as a second component in another embodiment. Each embodiment described and illustrated herein may also include a complementary embodiment. In addition, the term "and/or" is used herein to include at least one of the components listed before and after the term.

The singular expression herein includes a plural expression unless the context clearly specifies otherwise. In addition, it will be understood that the term such as "include" or "have" herein is intended to designate the presence of feature, number, step, component, or a combination thereof recited in the specification, and does not preclude the possibility of the presence or addition of one or more other features, numbers, steps, components, or combinations thereof. In addition, the term "connection" is used herein to include both indirectly connecting a plurality of components and directly connecting the components.

In addition, in the following description of the embodiments of the present invention, the detailed description of known functions and configurations incorporated herein will be omitted when it possibly makes the subject matter of the present invention unclear unnecessarily.

Figure 1:
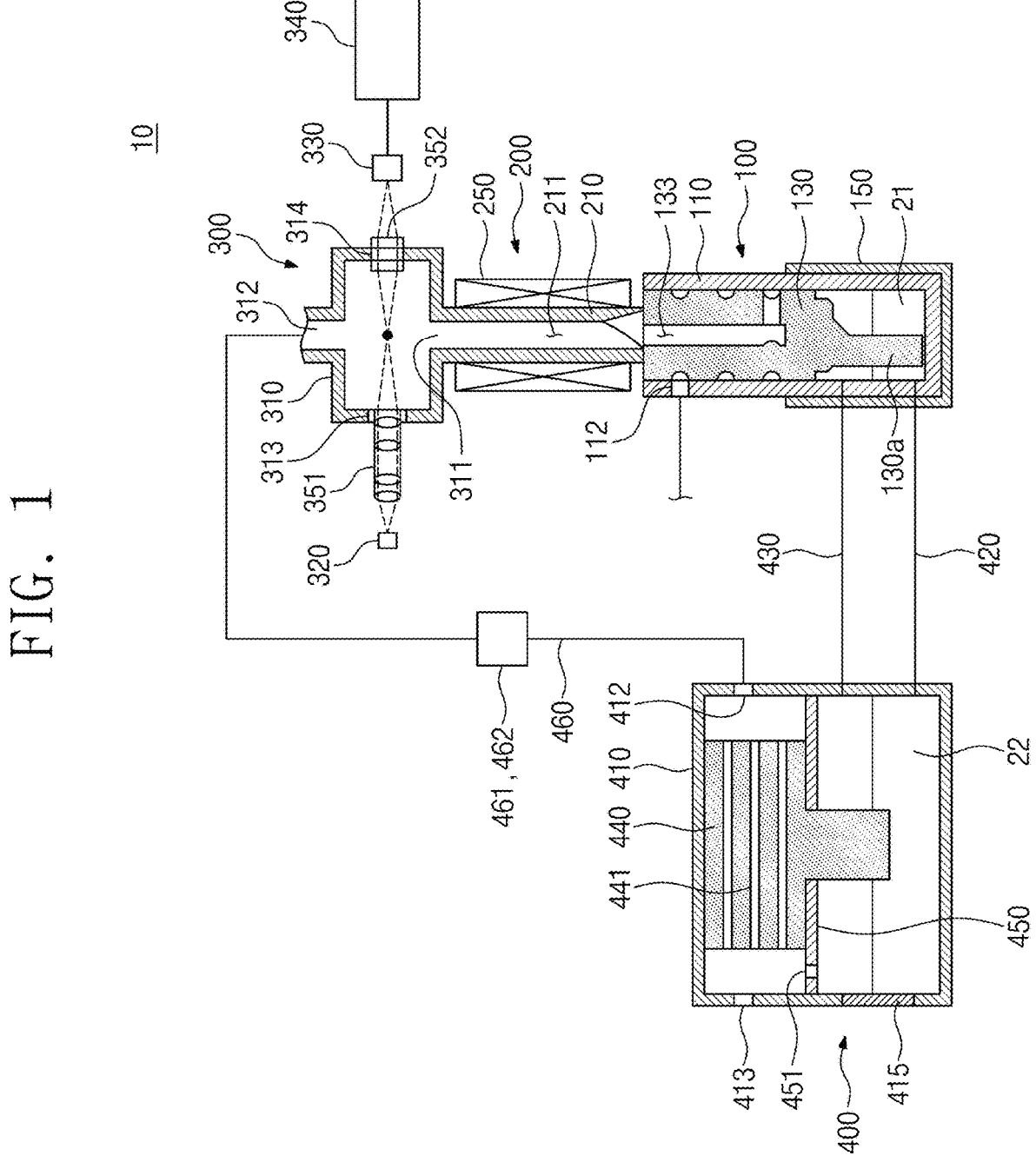
FIG. 1 is a view showing a condensation particle counter according to one embodiment of the present invention.

FIG. 1 is a view showing a condensation particle counter according to one embodiment of the present invention.

Referring to FIG. 1, the condensation particle counter 10 may supply vapor to the air until a saturated state, condense the vapor to create droplets having nano-particles contained in the air as condensation nuclei, and optically detect largely grown droplets, thereby measuring the number of nano-particles contained in the air.

The condensation particle counter 10 includes a saturator 100, a condenser 200, a detector 300 and a working fluid supply 400.

The saturator 100 supplies vapor to introduced air to saturate the air. The saturator 100 includes a saturation container 110, an absorber 130 and a heater 150.

The saturation container 110 is provided in a predetermined size and formed therein with a storage space. The storage space is filled with a working fluid 21 to a predetermined height. Water or alcohol may be used as the working fluid 21. According to the embodiment, water may be used as the working fluid. An air inlet 112 is formed at the top of the saturation container 110. The air inlet 112 is provided to serve as a passage through which air is introduced from the outside.

The absorber 130 is positioned within the saturation container 110. The absorber 130 is provided in a cylindrical shape as a whole, and has an outer diameter corresponding to an inner diameter of the saturation container 110. The absorber 130 is formed of a porous material. According to the embodiment, the absorber 130 may be formed of a non-woven fabric. The absorber 130 has a lower region 130*a* extending downward to a predetermined length and is submerged in the working fluid 21. Accordingly, the working fluid 21 is permeated and impregnated into the absorber 130.

FIG. 2 is a drawing showing an outer surface of the absorber according to one embodiment of the present invention. FIG. 3 is a sectional view showing the absorber of FIG. 2.

Referring to FIGS. 2 and 3, a first flow path 131 is formed in the absorber 130. The first flow path 131 provides a passage through which external air introduced into the air inlet 112 moves to the condenser 200. The first flow path 131 is designed to have a large contact area so that vapor may be sufficiently supplied while the air moves.

According to the embodiment, the first flow path 131 includes an outer flow path 132, an inner flow path 133, a first connection flow path 134 and a second connection flow path 135.

The outer flow path 132 is formed on the outer surface of the absorber 130 and formed in a ring shape along a circumference of the absorber 130. The outer flow path 132 is indented to a predetermined depth from the outer surface of the absorber 130, and may have a hemispherical section.

A plurality of outer flow paths 132 are formed from an upper end to a lower end of the absorber 130 and spaced apart at predetermined intervals. According to the embodiment, the absorber 130 is formed therein with three outer flow paths 132.

The inner flow path 133 is formed inside the absorber 130. The inner flow path 133 is formed in a central region of the absorber 130, and provided in a longitudinal direction of the absorber 130.

The first connection flow path 134 is formed on the outer surface of the absorber 130 to connect the adjacent outer flow paths 132 to each other. A plurality of first connection flow paths 134 are provided to connect different outer flow paths 132 to each other. The first connection flow paths 134 are positioned offset from each other in a vertical direction without being positioned on the same straight line.

The second connection flow path 135 connects an outer flow path 132 formed at the lowest portion of the outer flow paths 132 to the inner flow path 133.

The external air introduced into the air inlet 112 is primarily circulated around the absorber 130 along the outer flow path 132 formed at the top. According to the embodiment, some of the external air is circulated in a direction of one side of the absorber 130 along the outer flow path 132, and the remainder is circulated in a direction of an opposite side of the absorber 130 along the outer flow path 132. The air circulated on both sides meets at the upper portion of the first connection flow path 134, and moves to the outer flow path 132 formed in a middle section through the first connection flow path 134. The air is secondarily circulated through the absorber 130 through the above-described route along the outer flow path 132 formed in the middle section, and then moves to the outer flow path 132 formed in the lowermost section through the first connection flow path 134 connected thereto. The air is tertiarily circulated through the absorber 130 along the outer flow path 132 formed at the lowermost section, and then moves to the inner flow path 133 through the second connection flow path 135. The air moves from the bottom to the top of the inner flow path 133 and then moves to the condenser 200.

On the contrary, the outer flow path 132 may be formed in a spiral shape on the outer surface of the absorber 130, and connected to the inner flow path 133 through the second connection flow path 135. The external air introduced into the air inlet 112 rotates around the absorber 130 several times along the spiral flow path, and then moves to the inner flow path 133 through the second connection flow path 135. Due to the above-described design of the first flow path 131, the movement length of air may become longer and the contact area with the absorber 130 may be increased.

The heater 150 surrounds the saturation container 110 from the outside of the saturation container 110 to heat the inside of the saturation container 110 a predetermined temperature. The temperature inside the saturation container 110 is maintained at 35° C. to 60° C. due to the heating by the heater 150. When the inside of the saturation container 110 is maintained at the above-mentioned temperature, the working fluid 21 permeated in the absorber 130 evaporates.

Vapor generated by evaporating the working fluid 21 is mixed with air flowing along the first flow path 131. As described above, the movement length of air in the absorber 130 becomes long, so that the vapor can be sufficiently supplied. The air becomes saturated by supplying the vapor. The air in a saturated state moves to the condenser 200 through the inner flow path 133.

The condenser 200 is positioned at the upper portion of the saturator 100 to condense the saturated air supplied through the first flow path 131. The condenser 200 includes a condensation pipe 210 and a cooler 250.

The condensation pipe 210 is provided to have a predetermined length, and has a longitudinal direction arranged in the vertical direction. The condensation pipe 210 is formed therein with a second flow path 211.

The cooler 250 is provided on an outer side of the condensation pipe 210 to lower an internal temperature of the condensation pipe 210. The inside of the condensation pipe 210 is maintained at a temperature lower than that of the saturator 100 by controlling the temperature of the cooler 250. According to the embodiment, the internal temperature of the condensation pipe 210 is maintained at 3° C. to 10° C.

The saturated air has a decreased temperature while moving along the second flow path 211 and becomes supersaturated. The supersaturated vapor is condensed using particles contained in the air as condensation nuclei and grows into droplets. The droplet moves to the detector 300 along the air flow.

The detector 300 calculates the number of nano-particles contained in the air by optically detecting the droplets. The detector 300 includes a housing 310, a light source 320, a light detector 330, a signal analysis unit 340, and a plurality of lenses 351 and 352.

The housing 310 is formed therein with a space, and has an inlet 311 formed at the bottom thereof and an outlet 312 formed at the top thereof. The housing 310 is formed therein with openings, such as a light inlet 313 and a light detection port 314, in addition to the inlet 311 and the outlet 312. The housing 310 is connected to the condensation pipe 210, in which the air and the droplets are introduced through the inlet 311. The air and the droplets introduced into the housing 310 are exhausted to the outside through the outlet 312. The openings are provided with lenses 351 and 352, respectively.

The light source 320 is positioned on one side of the housing 310 to emit light into the housing 310 through the opening. The light emitted from the light source 320 is concentrated by the lens 351 provided on one side, collected by the lens 352 provided on the opposite side through the internal space of the housing 310 and then detected by the light detector 330. An optical signal is scattered by the droplets while passing through the internal space of the housing 310, and the scattered light is concentrated by the lens 352 and then detected by the light detector 330. The signal analysis unit 340 calculates the number of droplets by analyzing the scattered light signal among the signals detected by the light detector 330.

The working fluid supply 400 adjusts the vertical level of the working fluid 21 filled in the saturation container 110.

The working fluid supply 400 includes a storage tank 410, a first connection pipe 420, a second connection pipe 430, a vertical level control block 440, a support plate 450, and an air movement pipe 460.

The storage tank 410 is provided in a predetermined size, and formed therein with a storage space in which the working fluid 22 may can be stored. The working fluid 22 is stored in the storage tank 410 at a predetermined level.

An inlet 412 is formed on one side of the storage tank 410, and an outlet 413 is formed on an opposite side facing the inlet. The inlet 412 and outlet 413 are formed higher than the vertical level of the working fluid 22.

A viewing window 415 is provided in one side surface of the storage tank 410. A user can check a liquid level of the working fluid 22 in the storage tank 410 through the viewing window 415. When the flow rate of the working fluid 22 stored in the storage tank 410 is insufficient, the user may replenish a working fluid. In addition, a vertical level measurement sensor (not shown) may be provided inside the storage tank 410. The vertical level measurement sensor senses the liquid level of the working fluid 22 in the storage tank 410. Information measured by the vertical level measurement sensor may be provided to the user through an alarm or the like.

The first connection pipe 420 connects the storage tank 410 to the saturation container 110. The first connection pipe 420 has one end connected to a lower end portion of the storage tank 410 and an opposite end connected to a lower end portion of the saturation container 110. The first connection pipe 420 provides a passage through which the working fluids 21 and 22 stored in the storage tank 410 and the saturation container 110 move between the storage tank 410 and the saturation container 110. Accordingly, the vertical levels between the working fluid 22 in the storage tank 410 and the working fluid 21 in the saturation container 110 are maintained identical. When the flow rate of the working fluid 21 in the saturation container 110 is decreases as the working fluid 21 in the saturation container 110 is evaporated into vapor, the working fluid 22 in the storage tank 410 moves into the saturation container 110 through the first connection pipe 420. Accordingly, the working fluid 21 may be replenished in the saturation container 110.

The second connection pipe 430 connects the storage tank 410 to the saturation container 110 at a position higher than the first connection pipe 420. According to the embodiment, the second connection pipe 430 connects an upper space of the working fluid 21 stored in the saturated container 110 to an upper space of the working fluid 22 stored in the storage tank 410.

Since the air introduced into the condensation particle counter 10 contains water vapor, the amount of condensed water condensed in the condenser 200 may be greater than the amount of working fluid 21 evaporated in the evaporator 100 in some cases. For this reason, when the condensation particle counter 10 operates, the condensed water is supplied to the saturated container 110 through the absorber 130, the flow rate of the working fluid 21 in the saturation container 110 is increased, and the vertical level rises. As the vertical level of working fluid 21 is increased, the air remaining in the upper space of the working fluid 21 is moved to the storage tank 410 through the second connection pipe 430 and exhausted to the outside through a vent 451. Accordingly, the vertical level of the working fluid 21 in the saturated container 110 can stably rise.

The vertical level control block 440 is provided in a predetermined size, and positioned within the storage tank 410. Specifically, the vertical level control block 440 is positioned in the upper region within the storage tank 410, and may have some region immersed in the working fluid 22. The vertical level control block 440 is provided as a porous material. According to the embodiment, the vertical level control block 440 may be formed of the same material as the absorber 130. The vertical level control block 440 absorbs the working fluid 22 stored in the storage tank 410.

The vertical level control block 440 is formed therein with an internal flow path 441. The internal flow path 441 is formed in a direction from the one side of the storage tank 410 formed with the inlet 412 to the opposite side of the storage tank 410 formed with the outlet 413. The internal flow path 441 provides a passage through which the air introduced through the inlet 412 moves toward the outlet 413. A plurality of internal flow paths 441 may be provided.

The support plate 450 is positioned within the storage tank 410 to support the vertical level control block 440. The support plate 450 refers to a thin plate, and has the area corresponding to the internal space of the storage tank 410. The support plate 450 is positioned at a predetermined height from the liquid level of the working fluid 22. The support plate 450 is formed therein with the vent 451. The vent 451 provides a passage through which the air remaining between the liquid level of the working fluid 22 and the support plate 450 moves toward the outlet 413. When the vertical level of the working fluid 22 rises as the flow rate of the working fluid 22 stored in the storage tank 410 is increased, the air remaining between the liquid level of the working fluid 22 and the support plate 450 is exhausted to the outside through the vent 451. Accordingly, the vertical level of the working fluid 22 can rise stably.

Unlike the present invention, when the support plate 450 is not provided with the vent 451, the rise in level of the working fluid 22 is limited. Specifically, when the space between the liquid level of the working fluid 22 and the support plate 450 becomes narrow as the vertical level of the working fluid 22 rises, an internal pressure is increased so that the vertical level of the working fluid 22 cannot rise any longer.

The air movement pipe 460 connects the outlet 312 of the housing 310 to the inlet 412 of the storage tank 410. The air movement pipe 460 provides a passage through which air discharged from the housing 310 moves into the storage tank 410. The air movement pipe 460 may be provided with a flow meter 461 and a pump 462. The flow meter 461 measures the flow rate of the air moving through the air movement pipe 460, and the pump 462 provides power for the air to move along the air movement pipe 460.

The air supplied into the storage tank 410 through the air movement pipe 460 passes through the internal flow path 441 of the vertical level control block 440 and is exhausted to the outside through the outlet 413.

When the flow rate of the working fluid 21 in the saturation container 110 is increased and the vertical level thereof rises as the condensation particle counter 10 operates, a part of the working fluid 21 is introduced into the storage tank 410 through the first connection pipe 420, and accordingly, the flow rate of the working fluid 22 in the storage tank 410 is increased and the vertical level thereof rises. The vertical level of the working fluid 22 in the storage tank 410 rises to the same level as the vertical level of the working fluid 22 in the saturated container 11.

When the vertical level of the working fluid 22 in the storage tank 410 rises, a lower region of the vertical level control block 440 is submerged in the working fluid 22, and the working fluid 22 is absorbed into the vertical level control block 440. The working fluid 22 absorbed in the vertical level control block 440 is evaporated by the air moving along the internal flow path 441 and discharged to the outside through the outlet 413. This process continues until the lower region of the vertical level control block 440 is no longer submerged in the working fluid 22. Accordingly, the vertical level of the working fluid 22 may be adjusted to a height at which the lower region of the vertical level control block 440 is prevented from being submerged in the working fluid.

FIG. 4 is a sectional view showing an absorber according to another embodiment of the present invention.

Referring to FIG. 4, the inner flow path 133 may be provided as a plurality of micro-flow paths. The air introduced into the second connection flow path 135 passes through the micro-flow path 133 and flows into the second flow path 211. When the micro-flow path 133 is formed, the contact area with air may be expanded.

Figure 5:
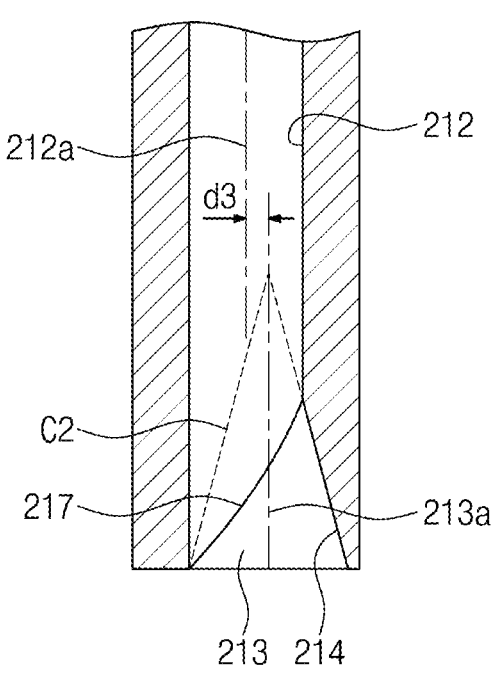
FIG. 5 is a sectional view showing a condensation pipe according to another embodiment of the present invention.
Figure 6:
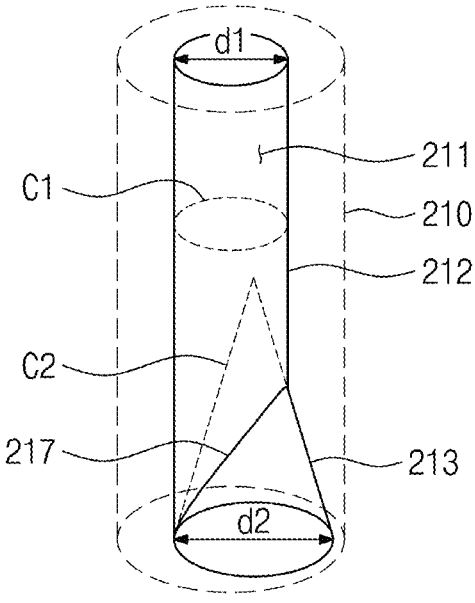
FIG. 6 is a perspective view showing a second flow path.
Figure 7:
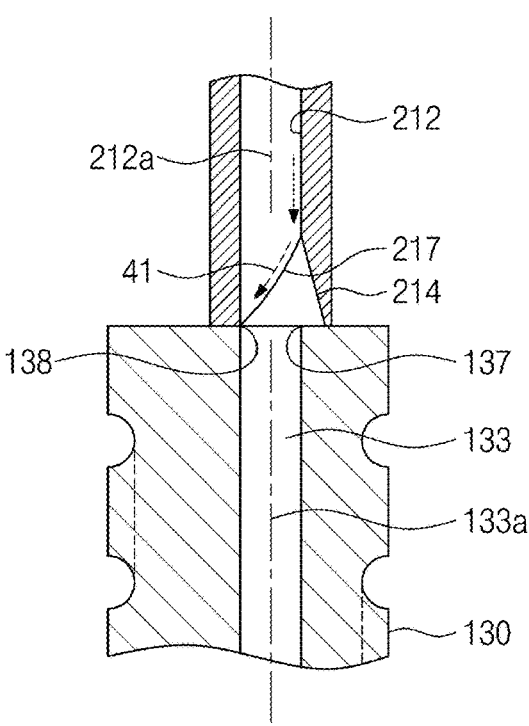
FIG. 7 is a view showing the arrangement of the condensation pipe and the absorber in FIG. 5.

FIG. 5 is a sectional view showing a condensation pipe according to one embodiment of the present invention. FIG. 6 is a perspective view showing the second flow path. FIG. 7 is a view showing the arrangement of the condensation pipe and the absorber in FIG. 5.

Referring to FIGS. 5 to 7, a guide portion 217 is formed on the inner surfaces 212 and 213 of the condensation pipe 210 defining the second flow path 211. In the process of condensing the saturated air within the second flow path 211, condensate is formed on the inner surface 212 of the second flow path 211, and the condensate flows down along the inner surface 212 of the second flow path 211 by gravity. The guide portion 217 guides the condensate flowing downward along the inner surface of the second flow path 211 to quickly flow into the absorber 130.

According to the embodiment, the second flow path 211 includes a first inner surface 212 and a second inner surface 213. The first inner surface 212 has a cylindrical shape C1. The second inner surface 213 is formed at a lower portion of the first inner surface 212 to define a bottom region of the second flow path 211.

According to the embodiment, The second inner surface 213 may be provided as one region of a cone shape C2.

In order to have the first inner surface 212 and the second inner surface 213, a machining process of the cylindrical shape C1 and a machining process of the cone shape C2 may be performed in the condensation pipe 210.

The central axis 212a of the cylindrical shape C1 and the central axis 213a of the conical shape C2 may be spaced apart at a predetermined distance without being positioned on the same straight line. In addition, a bottom surface of the cone shape C2 may have a diameter d2 larger than a diameter d1 of a bottom surface of the cylindrical shape C1 (d2>d1). Accordingly, a distance of the second inner surface 213 from the central axis 213a of the second inner surface 213 is gradually increased toward the bottom of the second flow path 211.

Through the cone-shaped processing, the second inner surface 213 has an inclined surface 214 on one side thereof inclined at a predetermined angle. In addition, the second inner surface 213 is provided asymmetrically about the central axis 212a of the second inner surface 213.

A boundary line 217 in which the first inner surface 212 meets the second inner surface 213 is provided as a curve. The boundary line 217 is inclined downward along a circumference of the first inner surface 212 from the top of the inclined surface 214. Based on the boundary line 217, the first inner surface 212 and the second inner surface 213 form a discontinuous surface.

The absorber 130 is positioned below the condensation pipe 210, in which the central axis 133a of the inner flow path 133 and the central axis 212a of the first inner surface 212 are arranged to be positioned on the same straight line. The inner flow path 133 has the same inner diameter as the first inner surface 212. Accordingly, a step 137 of the absorber 130 forming the inner flow path 133 is positioned on the inclined surface 214, and a step 138 of the absorber 130 is placed at the bottom of the boundary line 217.

Condensate 41 formed on the first inner surface 212 flows downward along the first inner surface 212, is guided by the boundary line 217 and gathers at the bottom of the boundary line 217. In addition, the condensate 41 is quickly absorbed into the absorber 130 through the step 138 of the absorber 130. As the above description, the boundary line 217, in which the first inner surface 212 meets the second inner surface 213, is provided as a guiding portion to guide the condensate 41 to quickly flow into the absorber 130.

Unlike the present invention, when the condensate is not quickly absorbed into the absorption part 130 and the collected state continues for a predetermined period of time, the size of the droplets is increased as the condensate is continuously introduced. In addition, the droplets are pushed back into the second flow path 211 due to friction with the air introduced through the inner flow path 133, thereby flowing into the housing 310. The droplets flowing into the housing 310 are condensed on the lenses 351 and 352 and cause interference with the operation of the detector 300.

According to the present invention, when the guide portion 217 is formed, so that the condensate may be prevented from flowing into the detector 300.

Figure 8:
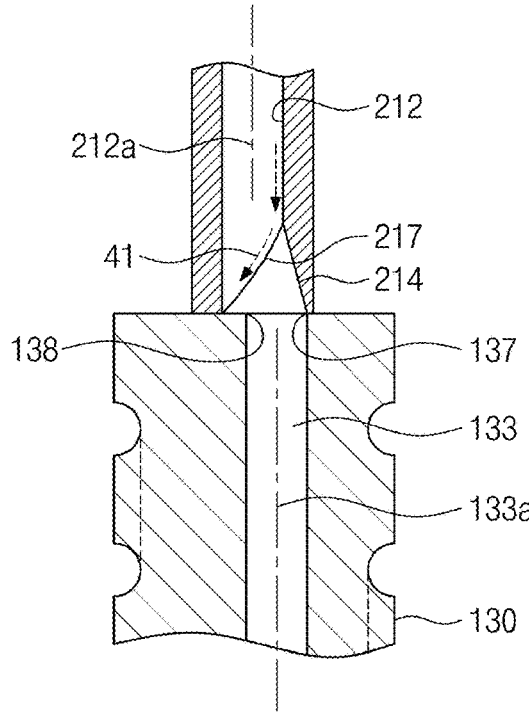
FIG. 8 is a view showing an absorber and a condensation pipe according to another embodiment of the present invention.

FIG. 8 is a view showing an absorber and a condensation pipe according to another embodiment of the present invention.

Referring to FIG. 8, the condensation pipe 210 is provided in the same way as the condensation pipe 210 described in FIGS. 5 and 6. The condensation pipe 210 is placed at the top of the absorber 130 so as to be offset by a predetermined distance, such that the central axis 212a of the first inner surface 212 and the central axis 133a of the inner flow path 133 are positioned on different straight lines. The lower end of the inclined surface 214 is positioned to come into contact with the step 137 of the absorber 130.

Condensate 41 formed on the first inner surface 212 flows downward along the first inner surface 212, is guided by the boundary line 217 and gathers at the bottom of the boundary line 217. Since the step 138 of the absorber 130 is positioned at the bottom of the boundary line 217 to have an area larger than an area of the step 138 of FIG. 7, the condensate 41 can be more quickly absorbed into the absorber 130.

Figure 9:
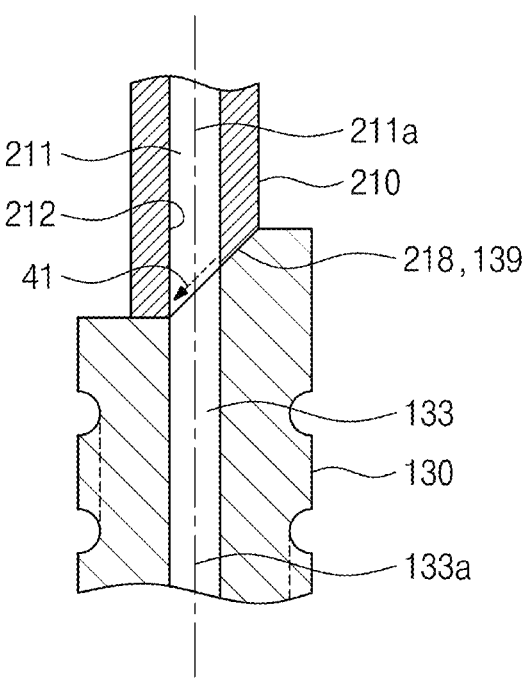
FIG. 9 is a view showing an absorber and a condensation pipe according to still another embodiment of the present invention.

FIG. 9 is a view showing an absorber and a condensation pipe according to still another embodiment of the present invention.

Referring to FIG. 9, the inner surface 212 of the second flow path 211 is provided in a cylindrical shape, and the condensation pipe 210 has a lower end cut obliquely. Accordingly, the condensation pipe 210 is provided with a bottom surface as an inclined surface 218 inclined at a predetermined angle.

The absorber 130 has one side of the top protruding to a predetermined height, in which an upper surface of the protruding region is provided as an inclined surface 139 corresponding to the inclined surface 218 of the condensation pipe 210. The condensation pipe 210 has the inclined surface 218 placed on the inclined surface 139 of the absorber 130. The condensation pipe 210 is placed on the top of the absorber 130 so that the central axis 211a of the second flow path 211 and the central axis 133a of the first flow path 133 are positioned on the same line.

The condensate 41 formed on the inner surface of the condensation pipe 210 flows downward by gravity, gathers on the inclined surface 214 of the condensation pipe 210, and flows downward along the inclined surface 214. In the above process, the condensate 41 is quickly absorbed into the inclined surface 139 of the absorber 130. Accordingly, the inclined surface 218 of the condensation pipe 210 serves as a guiding portion for guiding the condensate 41 to quickly flow into the absorber 130.

Figure 10:
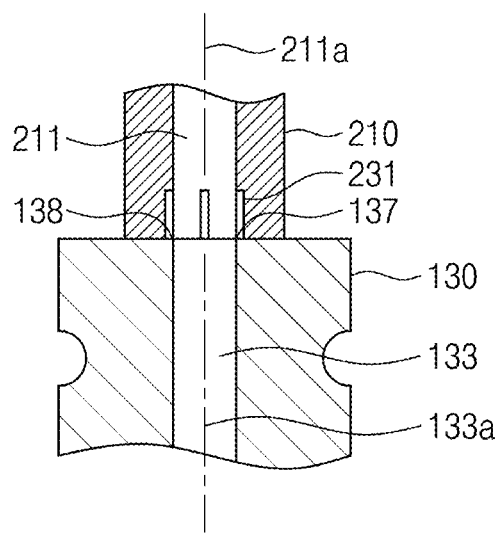
FIG. 10 is a view showing an absorber and a condensation pipe according to still another embodiment of the present invention.

FIG. 10 is a view showing an absorber and a condensation pipe according to still another embodiment of the present invention.

Referring to FIG. 10, the lower region of the condensation pipe 210 has an inner groove 231 formed on an inner surface thereof. The inner groove 231 is formed to have a predetermined length in the longitudinal direction of the second flow path 211 and extends to the bottom of the condensation pipe 210. The inner groove 231 is formed at a predetermined depth in a radial direction of the condensation pipe 210. A plurality of inner grooves 213 are formed along an inner circumferential surface of the second flow path 211 and spaced apart from each other. According to the embodiment, the condensation pipe 210 may be formed therein with four inner grooves 231. Spaces between the inner grooves 231 may be provided to be identical.

The condensation pipe 210 is placed on the top of the absorber 130, so that the central axis 211a of the second flow path 211 and the central axis 133a of the first flow path 133 are positioned on the same line. Accordingly, upper ends 137 and 138 of the absorber 130 defining the first flow path 133 are positioned at lower portions of the inner grooves 213.

The condensate formed on the inner surface of the condensation pipe 210 flows downward by gravity, gathers in the inner groove 231, and flows along the inner groove 231 so as to be quickly absorbed to the top of the absorber 130. Accordingly, the inner groove 231 formed in the condensation pipe 210 serves as a guiding portion for guiding the condensate to quickly flow into the absorber 130.

Figure 11:
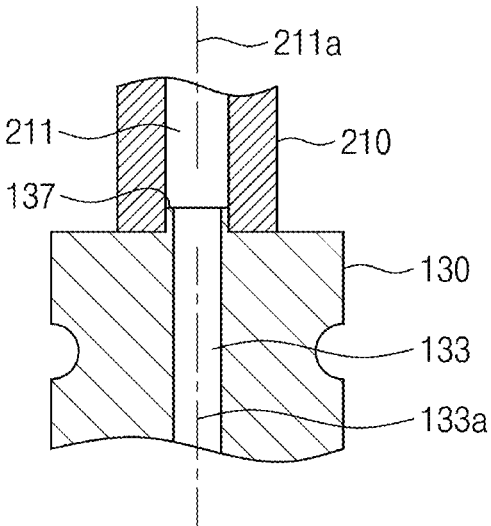
FIG. 11 is a view showing an absorber and a condensation pipe according to still another embodiment of the present invention.

FIG. 11 is a view showing an absorber and a condensation pipe according to still another embodiment of the present invention.

Referring to FIG. 11, a step 137 is formed at the top of the absorber 130. The step 137 protrudes from the upper surface of the absorber 130 at a predetermined height, and is formed in a ring shape. An outer diameter of the step 137 has a size corresponding to an inner diameter of the second flow path 211. The step 137 is inserted into the second flow path 211.

The condensate formed on the inner surface of the condensation pipe 210 flows downward by gravity and gathers on the step 137 of the absorber 130, and is quickly absorbed into the absorber 130 through the step 137. Accordingly, the step 137 of the absorber 130 is provided as a guiding portion for guiding the condensate to quickly flow into the absorber 130.

Figure 12:
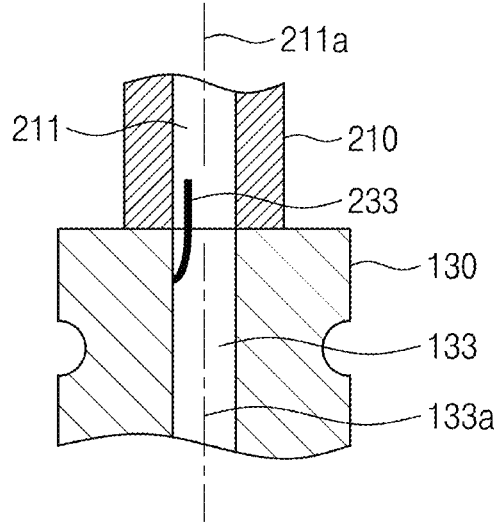
FIG. 12 is a view showing an absorber and a condensation pipe according to still another embodiment of the present invention.

FIG. 12 is a view showing an absorber and a condensation pipe according to still another embodiment of the present invention.

Referring to FIG. 12, a fiber 233 is attached to a lower region of the second flow path 211. The fiber 233 is provided to have a predetermined length, and may have an upper region attached to the inner surface of the second flow path 211 and a lower region attached to the inner surface of the inner flow path 133. According to another embodiment, a plurality of fibers 233 may be provided.

The condensate formed on the inner surface of the condensation pipe 210 flows downward by gravity and is absorbed into the fiber 233. The condensate is absorbed into the inner surface of the absorber 130 through the fiber 233.

Accordingly, the fiber 233 is provided as a guiding portion for guiding the condensate to quickly flow into the absorber 130.

Figure 13:
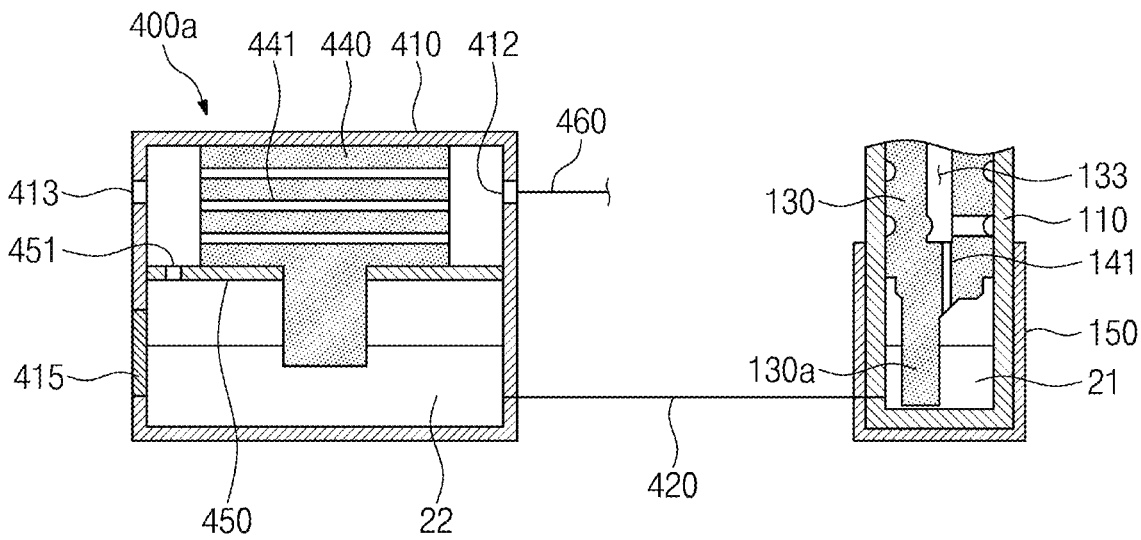
FIG. 13 is a view showing a working fluid supply and an absorber according to another embodiment of the present invention.

FIG. 13 This a view showing a working fluid supply and an absorber according to another embodiment of the present invention.

Referring to FIG. 13, a working fluid supply 400a is not provided with the second connection pipe 430 unlike the working fluid supply 400 described in FIG. 1.

An exhaust hole 141 is formed in the lower region of the absorber 130. The exhaust hole 141 connects an external space of the absorber 130 to the inner flow path 133.

When the condensed water condensed in the condensation pipe 210 is supplied into the saturation container 110 and the vertical level of the working fluid 21 in the saturation container 110 is increased, the air remaining in the upper space of the working fluid 21 moves to the inner flow path 133 through the exhaust hole 141. Accordingly, the vertical level of the working fluid 21 in the saturated container 110 may rise stably.

Figure 14:
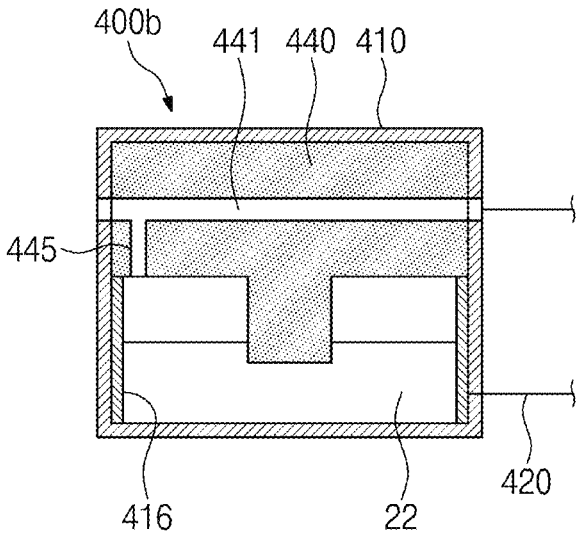
FIG. 14 is a view showing a working fluid supply according to still another embodiment of the present invention.

FIG. 14 is a view showing a working fluid supply according to still another embodiment of the present invention.

Referring to FIG. 14, a working fluid supply 400b is not provided with the support plate 450 (in FIG. 1), and the vertical level control block 440 has a sectional area corresponding to the storage space of the storage tank 410. The vertical level control block 440 may be supported by a support step 416 formed on the inner surface of the storage tank 410. The vertical level control block 440 is formed therein with a vent 445. The vent 445 connects a space between the vertical level control block 440 and the working fluid 22 to the internal flow path 441. When the vertical level of the working fluid 22 is increased, air in the space between the vertical level control block 440 and the working fluid 22 may be discharged to the outside through the vent 445. Accordingly, the vertical level of the working fluid 22 can be stably increased.

Figure 15:
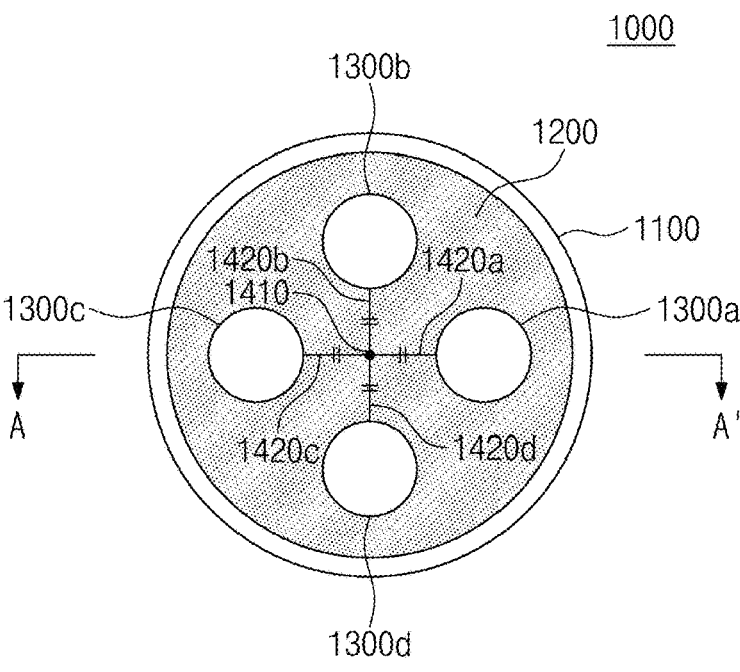
FIG. 15 is a plan view showing a condensation particle counting system according to the embodiments of the present invention.
Figure 16:
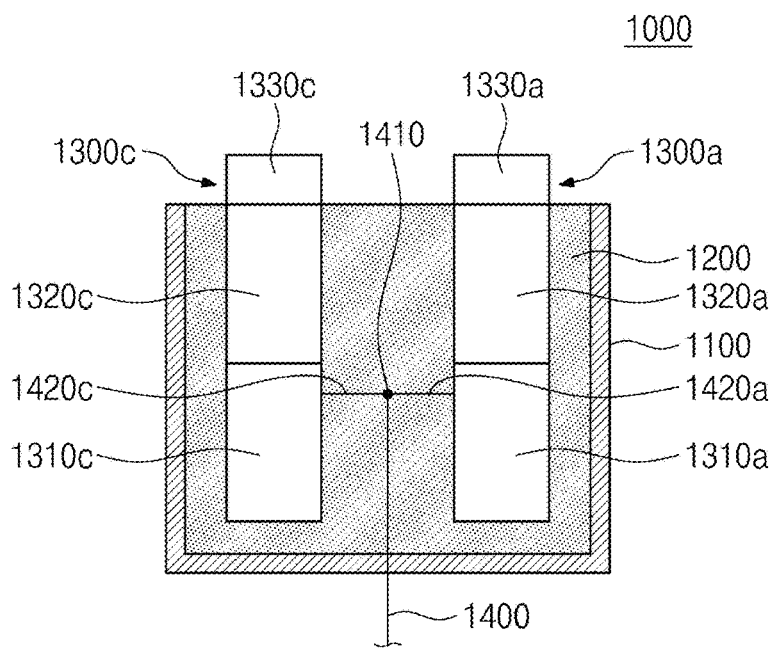
FIG. 16 is a sectional view showing the condensation particle counting system cut along line A-A' in FIG. 15.
Figure 17:
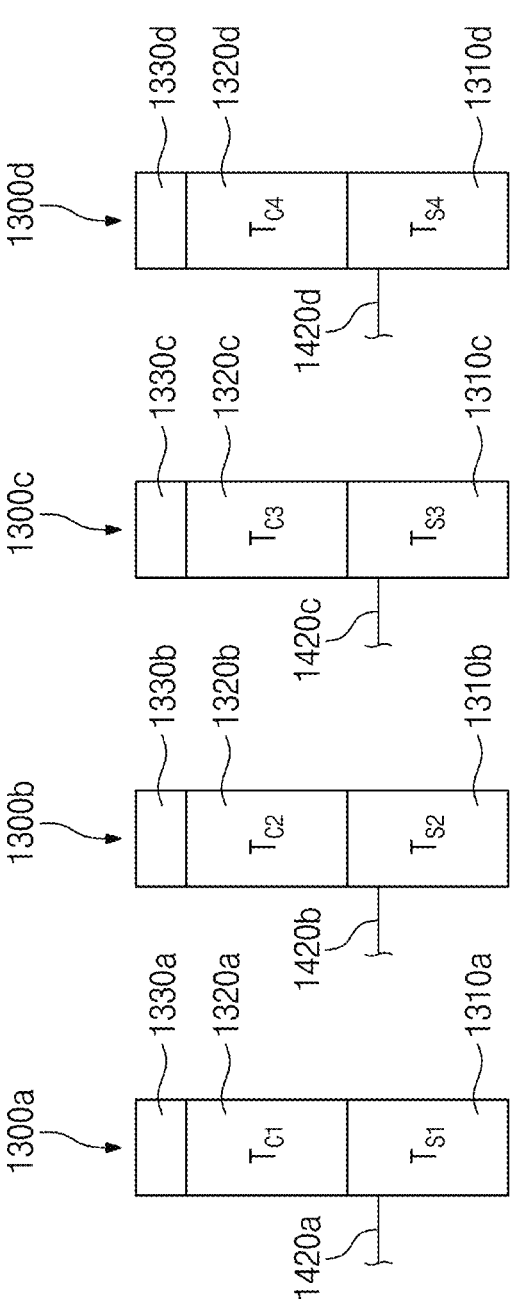
FIG. 17 is a view showing the condensation particle counters of FIG. 15.

FIG. 15 is a plan view showing the condensation particle counting system according to the embodiments of the present invention. FIG. 16 is a sectional view showing the condensation particle counting system cut along line A-A' in FIG. 15. FIG. 17 is a view showing the condensation particle counters of FIG. 15.

Referring to FIGS. 15 to 17, a condensation particle counting system 1000 may precisely measure sizes of nanoparticles contained in air using a plurality of condensation particle counters 1300a to 1300d. The condensation particle counting system 1000 includes a chamber 1100, condensation particle counters 1300a to 1300d, a working fluid supply (not shown), an air supply pipe 1400, and a control unit (not shown).

The chamber 1100 is provided in a predetermined shape, and formed therein with a receiving space. According to the embodiment, the chamber 1100 is provided in a cylindrical shape. An insulating material 1200 is provided in an internal space of the chamber 1100. The insulating material 1200 minimizes heat exchange inside and outside the chamber 1100.

The condensation particle counters 1300a to 1300d are positioned inside the chamber 1100, and surrounded by the insulating material 1200. A plurality of condensation particle counters 1300a to 1300d are provided. The condensation particle counters 1300a to 1300d are space apart at a predetermined distance from a central axis of the chamber 1100. According to the embodiment, the condensation particle counters 1300a to 1300d are positioned at the same distance from the central axis of the chamber 1100. The condensation particle counters 1300a to 1300d are spaced apart at predetermined intervals along the central axis of the chamber 1100. According to the embodiment, adjacent condensation particle counters 1300a to 1300d may be arranged at the same included angle about the central axis of the chamber 1100. According to the embodiment, four condensation particle counters 1300a to 1300d may be positioned in the chamber 1100, and arranged at an angle of 90° about the central axis of the chamber 1100.

The condensation particle counters 1300a to 1300d include saturators 1310a to 1310d, condensers 1320a to 1320d, and detectors 1330a to 1330d, respectively. Since the saturators 1310a to 1310d, the condensers 1320a to 1320d and the detectors 1330a to 1330d are provided in the same manner as the configurations described in FIGS. 1 to 13, the detailed description will be omitted.

The working fluid supply is connected to each of the condensation particle counters 1300a to 1300d to supply the working fluid to the saturators 1310a to 1310d. The working fluid supply may be provided in the same manner as any one of the working fluid supplies described in FIGS. 1, 13, and 14.

The air supply pipe 1400 is provided to have a predetermined length, and branched into a plurality of branch lines 1420a to 1420d starting from a branch point 1410. The branch lines 1420a to 1420d are connected to the saturators 1310a to 1310d of the condensation particle counters 1300a to 1300d, respectively, to supply external air into the saturators 1310a to 1310d. The branch lines 1420a to 1420d have the same length from the branch point 1410 to the saturators 1310a to 1310d. According to the embodiment, four branch lines 1420a to 1420d are formed in the air supply pipe 1400, the branch point 1410 is positioned on the central axis of chamber 1100, and the branch lines 1420a to 1420d are connected to the saturators 1310a to 1310d, respectively. The external air moving through the air supply pipe 1400 moves the same distance based on the branch point 1410 and flows into each of the saturators 1310a to 1310d.

The control unit may control such that the heating temperatures of the saturators 1310a to 1310d for each condensation particle counter 1300a to 1300d are different from each other, and may control such that the cooling temperatures of the condensers 1320a to 1320d are different from each other. The control unit may control such that the heating temperatures of the saturators 1310a to 1310d are different from each other in a temperature range of 35° C. to 60° C. In addition, the control unit may control such that the cooling temperatures of the condensers 1320a to 1320d are different from each other in a temperature range of 3° C. to 10° C.

According to the embodiment, the first saturator 1310a may be heated to a first heating temperature Ts1, the second saturator 1310b may be heated to a second heating temperature Ts2, the third saturator 1310c may be heated to a third heating temperature Ts3, and the fourth saturator 1310d may be heated to a fourth heating temperature Ts4. In addition, the first condenser 1320a may be cooled to a first cooling temperature Tc1, the second condenser 1320b may be cooled to a second cooling temperature Tc2, the third condenser 1320c may be cooled to a third cooling temperature Tc3, and the fourth condenser 1320d may be cooled to a fourth cooling temperature Tc4.

As described above, since the temperatures of the saturators 1310a to 1310d and the condensers 1320a to 1320d are independently controlled, the saturation degrees in the saturators 1310a to 1310d and the condensers 1320a to 1320d may be set differently. Accordingly, each of the detectors 1330a to 1330d may detect only particles of a predetermined size or larger.

The condensed droplets each contain one condensation particle, that is, one nano-particle. Whether the nano-particle acts as a condensation particle is determined by the Kelvin equation below [Equation 1].

$$\frac{P}{P_\infty} = S = \exp\left(\frac{4\sigma M}{D_P \rho_l RT}\right) \qquad \text{[Equation 1]}$$

Herein, $P_\infty$: vapor pressure at a distance from the particle, P: vapor pressure at a particle surface, S: saturation ratio, $\sigma$: surface tension of liquid, M: molecular weight of a liquid molecule, $D_P$: diameter of a nano-particle, $\rho_l$: density of liquid, R: gas constant, T: absolute temperature.

Based on Equation 1, it can be seen that sizes for allowing nano-particles to act as condensation nuclei vary depending on the saturation degree of the vapor. Equation 1 is expressed in the graph shown in FIG. 18.

Figure 18:
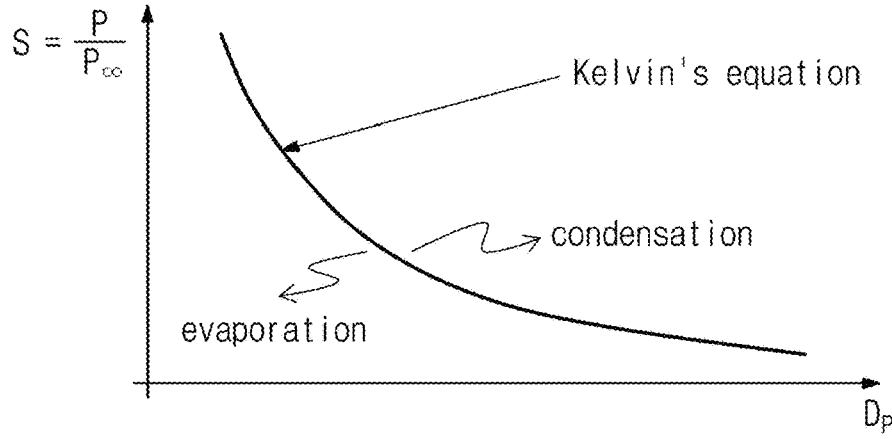
FIG. 18 is a graph representing a Kelvin equation.

Referring to FIG. 18, when an S value (saturation degree) of the vapor in the condenser is present above a Kelvin equation curve at a specific particle size (i.e. x=constant), the specific particle can be condensed and continue to grow, and conversely, when the S value is present below the Kelvin equation curve, the particle cannot act as a condensation particle. Accordingly, specific particles may be allowed to act as condensation nuclei and grow into droplets depending on the value of S, and the droplets may be detected optically, so that only particles over a specific size can be measured.

The present invention the saturation degree of each of the condensers 1320a to 1320d may be differently set by using the above-mentioned principle, to allow only particles having different sizes or larger for each condenser to grow into droplets and detects the grown particles, so that the sizes of nano-particles can be measured precisely.

In addition, the external air supplied through one air supply pipe 1400 is divided and flows into each of the branch lines 1420a to 1420d, moves the same distance from the branch point 1410, and is supplied into the saturators 1310a to 1310d, so that the loss of nano-particles contained in the external air may be minimized, and the amount of loss for all four saturators 1310a to 1310d may be the same.

Figure 19:
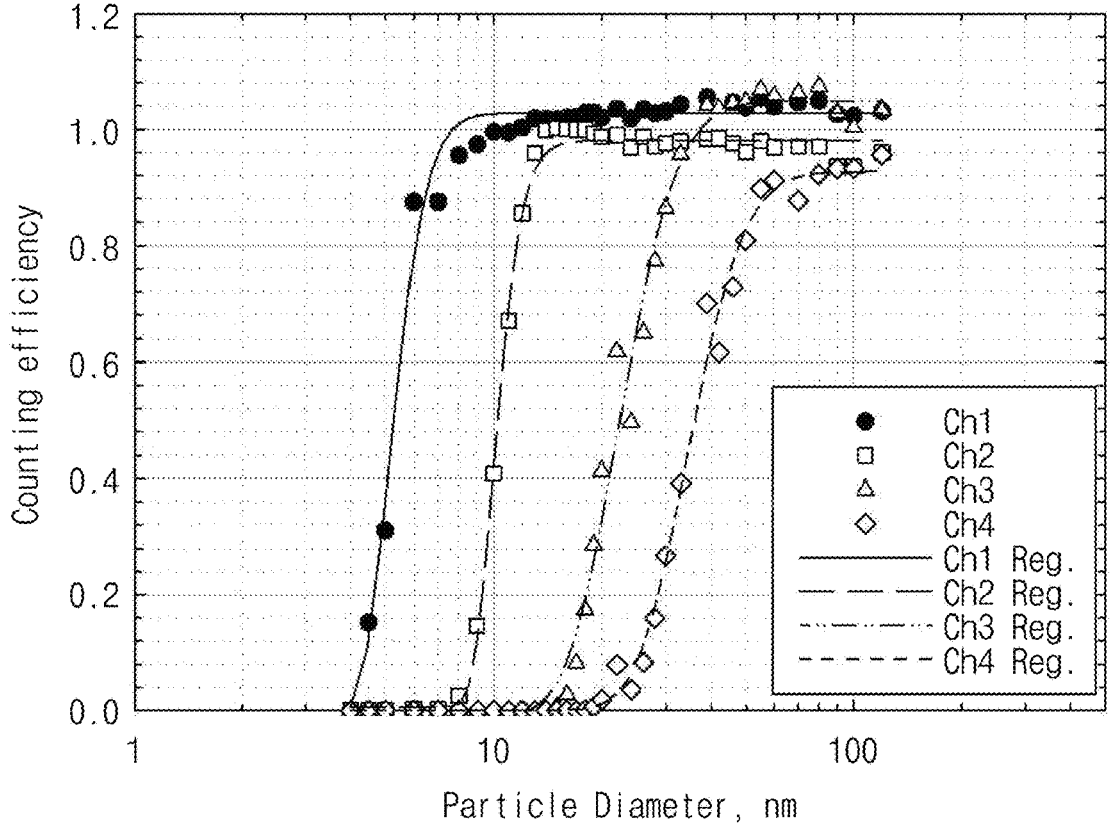
FIG. 19 is a graph obtained by measuring nano-particles in the air according to sizes by using the condensation particle counting system in FIG. 15.

FIG. 19 is a graph obtained by measuring nano-particles in the air according to sizes by using the condensation particle counting system in FIG. 15. A horizontal axis represents particle diameters of measured particles, and a vertical axis represents counting efficiency.

Referring to FIG. 19, each of the detectors 1330a to 1330d may measure only nano-particles of different sizes or larger, and accurately calculate sizes of the measured nano-particles.

In addition, in the condensation particle counting system 1000 according to the embodiments of the present invention, the measurement speed of nano-particle size distribution is 0.1 second, and this is a significant improvement in the measurement speed compared to the existing condensation particle counters, which takes at least 1 to 2 minutes to measure the nano-particle size distribution.

Although the present invention has been described in detail by using exemplary embodiments, the scope of the present invention is not limited to the specific embodiments, and will be interpreted by the appended claims. In addition, it will be apparent that a person having ordinary skill in the art may carry out various deformations and modifications for the embodiments described as above within the scope without departing from the present invention.

What is claimed is:

1. A condensation particle counter comprising:

a saturator formed therein with a first flow path for supplying vapor to air introduced from outside;

a condenser formed therein with a second flow path in which the air and the vapor introduced from the first flow path are condensed; and a detector for detecting droplets condensed in the condenser, wherein the second flow path is provided with a guiding portion for guiding condensate flowing downward along an inner surface of the second flow path to flow into the saturator, wherein the inner surface of the second flow path includes:

a first inner surface having a cylindrical shape; and a second inner surface positioned between the first inner surface and the first flow path and provided as a curved surface different from the first inner surface, and wherein the guiding portion includes a boundary line between the first inner surface and the second inner surface.

2. The condensation particle counter of claim 1, wherein the boundary line includes a curve inclined downward from one side of the second inner surface to an opposite side of the second inner surface.

3. The condensation particle counter of claim 1, wherein a central axis of the first inner surface and a central axis of the second inner surface are spaced apart and offset from each other at a predetermined distance.

4. The condensation particle counter of claim 1, wherein the second inner surface is asymmetric with respect to a central axis of the second inner surface.

5. The condensation particle counter of claim 1, wherein the second inner surface has a distance from a central axis of the second inner surface so as to be gradually increased toward a bottom of the second flow path.

6. The condensation particle counter of claim 1, wherein the saturator has a step provided below the second inner surface.

7. The condensation particle counter of claim 1, wherein the guiding portion includes an inner groove formed in a lower region of the second flow path in a longitudinal direction of the second flow path, in which the inner groove extends to a lower end of the second flow path.

8. The condensation particle counter of claim 1, wherein the guiding portion includes a step of the saturator inserted into a lower end of the second flow path.

9. The condensation particle counter of claim 1, wherein the guiding portion includes a fiber for connecting an inner side of the first flow path to an inner side of the second flow path.

10. The condensation particle counter of claim 1, wherein the saturator includes:

a saturation container formed therein with a space for storing a working fluid;

an absorber positioned inside the saturation container and formed of a first porous material by which the first flow path is formed; and a heater provided outside the saturation container to heat the saturation container, wherein the first flow path includes:

an outer flow path formed on an outer surface of the absorber along a circumference of the absorber;

an inner flow path formed in a central region of the absorber in a longitudinal direction of the absorber; and a first connection flow path for connecting the outer flow path to the inner flow path.

11. The condensation particle counter of claim 10, wherein the outer flow path is formed in a ring shape and provided with a plurality of outer flow paths spaced apart at predetermined intervals in the longitudinal direction of the absorber, and the first flow path further includes a second connection flow path for connecting the plurality of outer flow paths to each other.

12. The condensation particle counter of claim 11, wherein the absorber has a lower region submerged in the working fluid, and the lower region of the absorber is formed therein with an exhaust hole for connecting the inner flow path to an external space of the absorber.

13. The condensation particle counter of claim 10, further comprising:

a storage tank provided therein with the working fluid and having an inlet and an outlet formed at points higher than the working fluid;

a first connection pipe for providing a third flow path through which the working fluid moves between the storage tank and the saturation container;

a vertical level control block positioned in the storage tank and formed of a second porous material capable of absorbing the working fluid; and an air supply pipe for supplying air discharged from the detector to the inlet.

14. The condensation particle counter of claim 13, wherein the vertical level control block is formed therein with an internal flow path communicating with the inlet and the outlet.

15. The condensation particle counter of claim 14, wherein the vertical level control block is formed therein with a vent for connecting a lower space of the vertical level control block to the internal flow path.

16. A condensation particle counting system comprising:

a first condensation particle counter;

a second condensation particle counter; and a control unit configured to individually control the first condensation particle counter to a first temperature and the second condensation particle counter to a second temperature that is different from the first temperature, wherein the first condensation particle counter and the second condensation particle counter each includes:

a saturator for heating an inside thereof to a saturator heating temperature to generate vapor and supply the vapor to air introduced from outside the respective condensation particle counter; and a condenser for cooling an inside thereof to a condenser colling temperature to condense the air and the vapor introduced from the saturator, wherein the first temperature and the second temperature are both different from the saturator heating temperature and the condenser cooling temperature.

17. The condensation particle counting system of claim 16, further comprising:

an air supply pipe having a plurality of branch lines branched at a branch point, in which each of the plurality of branch lines is individually connected to the saturator to supply external air, wherein each of the plurality of branch lines is provided with an identical length from the branch point to the saturator.

18. The condensation particle counting system of claim 16, further comprising:

a chamber with insulating materials provided therein, wherein the first condensation particle counter and the second condensation particle counter are provided between the insulating materials, and wherein the first condensation particle counter and the second condensation particle counter are each positioned at an identical distance from a central axis of the chamber.

\* \* \* \* \*